(12) United States Patent
Stoecker

(10) Patent No.: US 11,903,990 B2
(45) Date of Patent: Feb. 20, 2024

(54) COMPOSITIONS AND METHODS FOR TREATING AND REMOVING SEBORRHEIC KERATOSES

(71) Applicant: William Van Dover Stoecker, Rolla, MO (US)

(72) Inventor: William Van Dover Stoecker, Rolla, MO (US)

( * ) Notice: Subject to any disclaimer, the term of this patent is extended or adjusted under 35 U.S.C. 154(b) by 106 days.

(21) Appl. No.: 17/576,922

(22) Filed: Jan. 15, 2022

(65) Prior Publication Data
US 2022/0133828 A1    May 5, 2022

Related U.S. Application Data

(62) Division of application No. 15/890,055, filed on Feb. 6, 2018, now abandoned.

(60) Provisional application No. 62/575,031, filed on Oct. 20, 2017, provisional application No. 62/455,559, filed on Feb. 6, 2017.

(51) Int. Cl.
| | |
|---|---|
| *A61K 36/52* | (2006.01) |
| *A61K 36/53* | (2006.01) |
| *A61K 36/484* | (2006.01) |
| *A61P 17/12* | (2006.01) |
| *A61K 31/122* | (2006.01) |
| *A61K 45/06* | (2006.01) |
| *A61K 9/00* | (2006.01) |
| *A61K 36/82* | (2006.01) |
| *A61K 36/752* | (2006.01) |
| *A61K 36/07* | (2006.01) |
| *A61K 47/10* | (2017.01) |
| *A61K 36/9066* | (2006.01) |
| *A61K 36/324* | (2006.01) |
| *A61K 9/06* | (2006.01) |
| *A61K 36/185* | (2006.01) |
| *A61K 47/46* | (2006.01) |

(52) U.S. Cl.
CPC ............ *A61K 36/52* (2013.01); *A61K 9/0014* (2013.01); *A61K 9/06* (2013.01); *A61K 31/122* (2013.01); *A61K 36/07* (2013.01); *A61K 36/185* (2013.01); *A61K 36/324* (2013.01); *A61K 36/484* (2013.01); *A61K 36/53* (2013.01); *A61K 36/752* (2013.01); *A61K 36/82* (2013.01); *A61K 36/9066* (2013.01); *A61K 45/06* (2013.01); *A61K 47/10* (2013.01); *A61K 47/46* (2013.01); *A61P 17/12* (2018.01)

(58) Field of Classification Search
None
See application file for complete search history.

(56) References Cited

U.S. PATENT DOCUMENTS

| | | | |
|---|---|---|---|
| 5,137,717 | A | 8/1992 | Wixforth |
| 5,859,066 | A | 1/1999 | Rosen |
| 7,357,950 | B2 | 4/2008 | Mazzio et al. |
| 7,829,067 | B2 | 11/2010 | D'Amelio, Sr. et al. |
| 8,206,755 | B2 | 6/2012 | Mtchedlidze |
| 8,481,006 | B2 | 7/2013 | Patnode |
| 2002/0127256 | A1* | 9/2002 | Murad .................. A61K 36/48 514/3.3 |
| 2003/0007939 | A1 | 1/2003 | Murad |
| 2004/0137077 | A1 | 7/2004 | Ancira et al. |
| 2008/0152603 | A1 | 6/2008 | Rudolph et al. |
| 2009/0131375 | A1 | 5/2009 | Gross |
| 2014/0315995 | A1 | 10/2014 | Dreher |
| 2016/0250181 | A1 | 9/2016 | Rosen |

FOREIGN PATENT DOCUMENTS

| | | |
|---|---|---|
| EP | 1231928 B1 | 6/2003 |
| WO | 2006/040596 A2 | 4/2006 |

OTHER PUBLICATIONS

Buckhart et al., Use of a keratolytic agent with occlusion for topical treatment of hyperkeratotic seborrheic keratoses, 2008, Skinmed, 7: 15-8.*
International Search Report and Written Opinion, PCT/US18/17092, dated Apr. 23, 2018.
Burdock, G.A., Safety Assessment of Hydroxypropyl Methylcellulose as a Food Ingredient, 2007, Food and Chemical Toxicology, 45:2341-2345.
Zaveri NT. Green tea and its polyphenolic catechins: medicinal uses in cancer and noncancer applications. Life Sci. 2006;78(18):2073-2080. [PMID 16445946].
Tzellos TG, Sardeli C, Lallas A, Papazisis G, Chourdakis M, Kouvelas D. Efficacy, safety and tolerability of green tea catechins in the treatment of external anogenital warts: a systematic review and meta-analysis. J Eur Acad Dermatol Venereol. Mar. 2011,25(3):345-53. [PMID: 21294779].
Tyring SK. Effect of Sinecatechins on HPV-Activated Cell Growth and Induction of Apoptosis. J Clin Aesthet Dermatol. Feb. 2012;5(2):34-41. [PMID: 22468171].
Turrini E, Ferruzzi L, Fimognari C. Potential Effects of Pomegranate Polyphenols in Cancer Prevention and Therapy. Oxid Med Cell Longev. 2015;2015:938475. doi: 10.1155/2015/938475. [PMID: 26180600].

(Continued)

*Primary Examiner* — Terry A McKelvey
*Assistant Examiner* — Catheryne Chen
(74) *Attorney, Agent, or Firm* — Hoffmann & Baron LLP; Edward K Welch, II

(57) ABSTRACT

A method of diminishing the appearance of or effecting the removal or disappearance of seborrheic keratoses by the application of compositions containing a) one or more, preferably a combination of, dietary antioxidants and/or antioxidant sources, b) one or more hydrating agents and c) one or more keratolytic agents.

20 Claims, 6 Drawing Sheets

(56) References Cited

OTHER PUBLICATIONS

Sreekumar S, Sithul H, Muraleedharan P, Azeez JM, Sreeharshan S. Pomegranate Fruit as a Rich Source of Biologically Active Compounds. Biomed Res Int. 2014; doi: 10.1155/2014/686921 [PMID: 24818149].

Rašković A, Milanović I, Pavlovic N, Ćebović T, Vukmirović S, Mikov M. Antioxidant activity of rosemary (*Rosmarinus officinalis* L.) essential oil and its hepatoprotective potential. BMC Complement Altern Med. Jul. 7, 2014;14:225. [PMID: 25002023].

Neel VA, Todorova K, Wang J, Kwon E, Kang M, Liu Q, Gray N, Lee SW, Mandinova A. Sustained Akt activity is required to maintain cell viability in seborrheic keratosis, a benign epithelial tumor. J Invest Dermatol. 2016;136(3):696-705. doi: 10.1016/j.jid.2015.12.023. [PMID: 26739095].

Lodén M/ The clinical benefit of moisturisers. J Eur Acad Dermatol Venereol 2005;19(6): 672-88. [PMID: 16268870].

Jacobi A, Mayer A, Augustin M. Keratolytics and emollients and their role in the therapy of psoriasis: a systematic review. Dermatol Ther (Heidelb). 2015;5(1):1-18. [PMID: 25604924].

Higdon JV, Frei B. Tea catechins and polyphenols: health effects, metabolism, and antioxidant functions. Crit Rev Food Sci Nutr. 2003;43(1):89-143. [PMID: 12587987].

Fluhr JW, Cavallotti C, Berardesca E. Emollients, moisturizers, and keratolytic agents in psoriasis. Clin Dermatol. 2008;26(4):380-386. [PMID: 18691519].

Davies M, Marks R. Studies on the effect of salicylic acid on normal skin. Studies on the effect of salicylic acid on normal skin. Br J Dermatol. Aug. 1976;95(2):187-92. [PMID: 952756].

DeFazio J, Zalaudek I, Busam KJ, Cota C, Marghoob A. Association between melanocytic neoplasms and seborrheic keratosis: more than a coincidental collision? Dermatol Pract Concept. Apr. 30, 2012;2(2):202a09. doi: 10.5826/dpc.0202a09 [PMID: 23785597].

Cabrera C, Artacho R, Gimenez R. Beneficial effects of green tea—a review. J Am Coll Nutr. 2006;25(2):79-99. [PMID: 16582024].

Egawa M. In vivo simultaneous measurement of urea and water in the human stratum corneum by diffuse-reflectance hear-infrared spectroscopy. Skin Res Technol. 2009;15(2):195-199. [PMID: 19622130].

Vuong QV, Golding JB, Nguyen M, Roach PD. Extraction and isolation of catechins from tea. J Sep Sci. 2010;33(21):3415-3428.

Piquero-Casals, et al., Urea in Dermatology: A Review of its Emollient, Moisturizing, Keratolytic, Skin Barrier Enhancing and Antimicrobial Properties, Dermatol. Ther. (Heidelb), 2021, 1905-1915.

\* cited by examiner

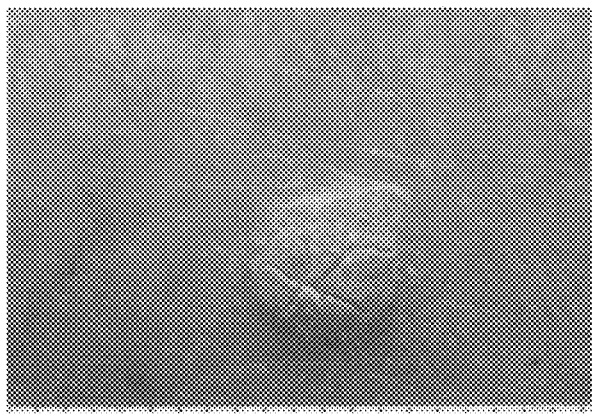
Fig. 5A Day 1: Left lateral thigh SK pre-treatment
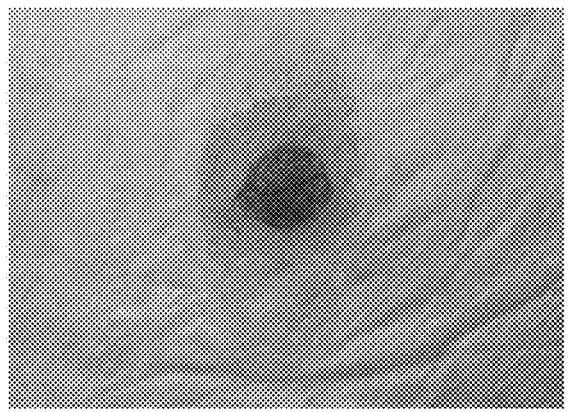
Fig. 5B Day 8: Thigh SK pre- keratin debris removal
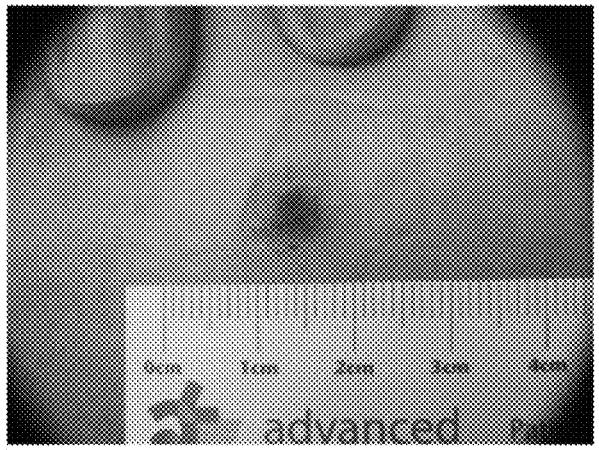
Fig. 5C Day 17: Thigh SK pre- keratin debris removall
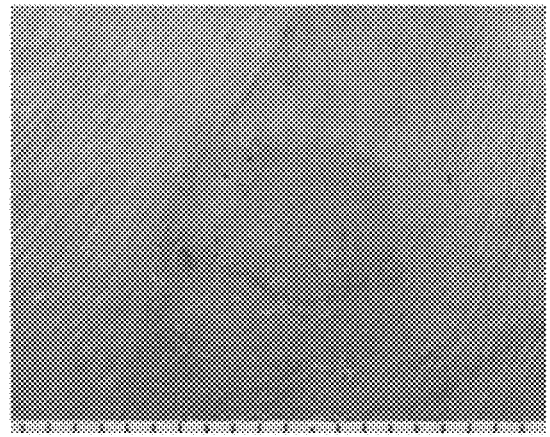
Fig. 5D Day 17: Thigh SK post- keratin debris removall

Fig. 6A Day 1: Lateral abdomen SK pre-treatment
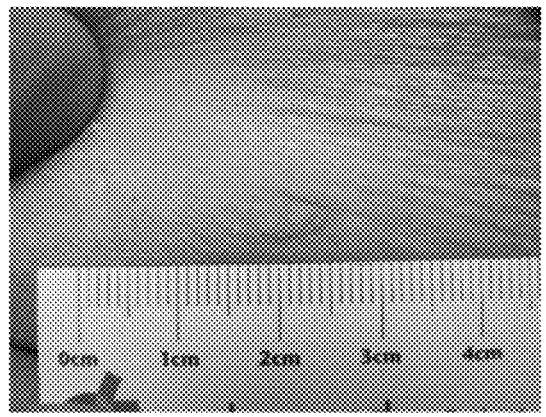
Fig. 6B Day 8: Lateral abdomen SK after keratin debris removal
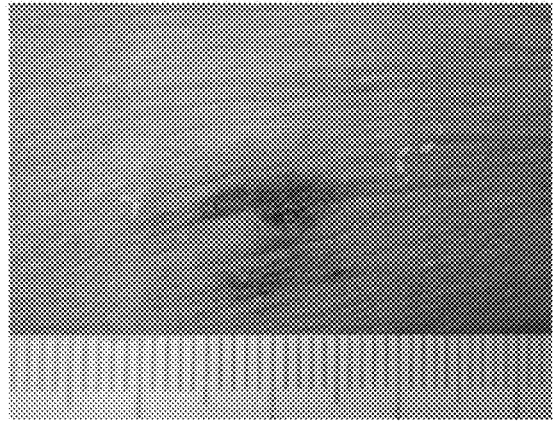
Fig. 6C Day 14: Lateral abdomen SK after 2$^{nd}$ keratin debris removal
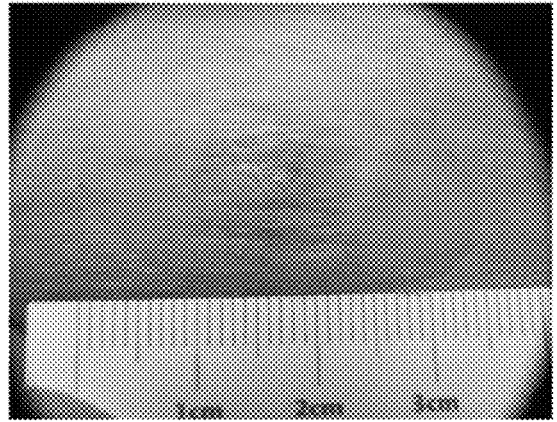
Fig. 6D. Day 17: Lateral abdomen SK after 3 days healing

Fig. 7A Day 1: Right calf SK pre-treatment
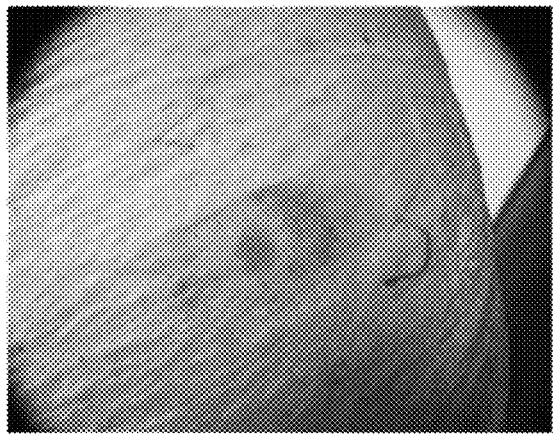
Fig. 7B Day 8: Right calf SK pre- keratin debris removal
Fig. 7C Day 15: Right calf SK healing. No further therapy was used.
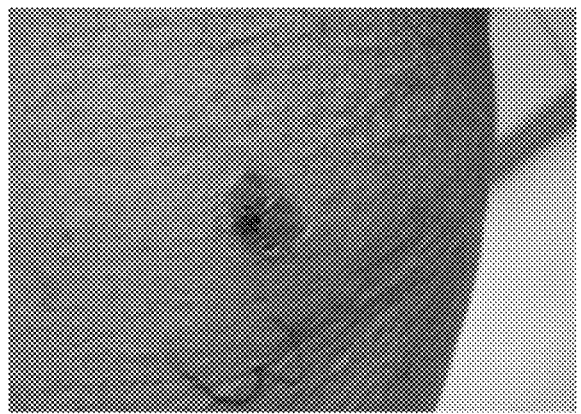
Fig. 7D Day 17: Thigh SK post- keratin debris removal
Fig. 7E Day 63: Right calf SK after treatment

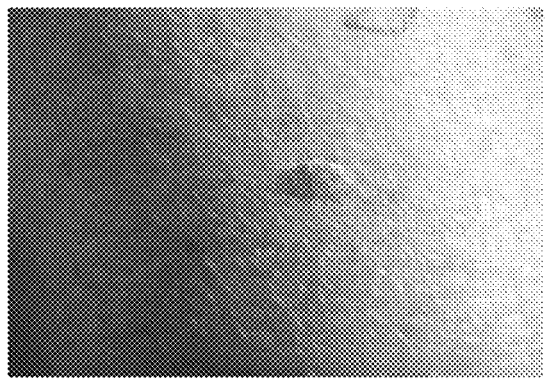
Fig. 8A Day 1: Right superior popliteal area SK
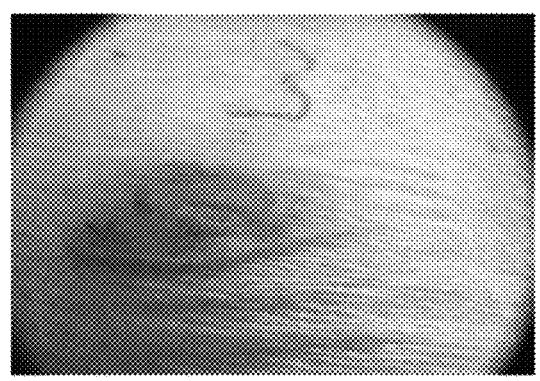
Fig. 8B Day 8: Right superior popliteal area SK
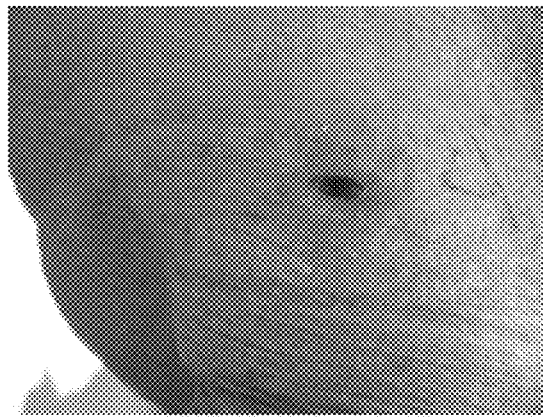
Fig. 8C Day 15: Right superior popliteal area post debridement
Fig. 8D Day 63 Right superior popliteal area SK after treatment

COMPOSITIONS AND METHODS FOR TREATING AND REMOVING SEBORRHEIC KERATOSES

RELATED APPLICATIONS

The present application is a divisional application of pending U.S. patent application Ser. No. 15/890,055 filed Feb. 6, 2018, which claims the benefit and priority of previously filed U.S. Provisional Application No. 62/455,559 filed Feb. 6, 2017 and 62/575,031 filed Oct. 20, 2017, both having the same title and inventor as the instant application, the contents of which are hereby incorporated herein by reference in their entirety.

FIELD OF THE INVENTION

The present invention relates to compositions and methods with which to treat and reduce, if not remove, seborrheic keratoses from the skin. Specifically, the application of specific topical compositions containing select antioxidants, especially dietary antioxidants, to skin manifesting seborrheic keratosis has been found to diminish the manifestation of the seborrheic keratosis as well as facilitate, if not cause, the exfoliation of seborrheic keratoses from the skin. In addition, the combination these select antioxidants with other skin enhancing/remedial additives, most especially hydrating/humectant agents and/or keratolytic agents, are found to supplement and/or promote the effect of the select dietary antioxidants as well as to counteract and/or mask irritation and skin damage that may arise therefrom.

BACKGROUND OF THE INVENTION

Seborrheic keratosis (SK) is a type of non-cancerous growth or tumor of the epidermis or outer layer of the skin. There is no single cause for the manifestation of seborrheic keratosis though heredity, sun exposure, and the like are believed to play some role. Two genes, including FGFR3 and PIK3CA, may play a role in SK development. Mutations in these genes also are associated with SKs (Berman and Zacharias). Seborrheic keratoses typically begin to appear later in life, especially as one ages through their 40s and into their 50s. These tumors, or lesions as they are oftentimes referred to, are commonly characterized as having the appearance of wax or a wax-like substance on the skin and typically range in size from very small to an inch or more in diameter: though they are not necessarily round.

Although there is some indication that seborrheic keratosis may lead or progress to squamous cell carcinoma, for the most part, these lesions are benign and harmless. Still, depending upon the location, color, size, etc. of the tumors, they can be unsightly. Additionally, they may become itchy or periodically bleed, especially if the tumor or tumors are in areas prone to the rubbing of fabric and the like. In these instances, individuals oftentimes seek to have the tumors removed: again, more as an aesthetic treatment than a medical treatment. Finally, because these tumors can take on the appearance of other skin maladies, including melanoma or squamous cell carcinoma, it is sometimes desirable to remove the tumor to remove the risk and, if truly of concern, to have the tumor examined to rule out melanoma.

There are several treatments or methods for the removal of seborrheic keratosis including cryosurgery where the tumor is frozen with liquid nitrogen and then allowed to slough off, curettage where special instruments are used to scrape off or thinly shave off the tumor; electrodessication where the tumor is burned off with an electric current, and ablation where the tumor is vaporized through different types of laser treatments as well as select combinations of the foregoing. All of these are expensive and are, and in many instances must be, administered by a medical professional.

Recently, there has been some movement towards the use of silver, specifically colloidal silver solutions and gels, in the treatment of seborrheic keratosis; however, the effectiveness is still under investigation and, in any event, topical application can and oftentimes does lead to skin discoloration in the treated area and oral consumption can lead to argyria where the whole of one's skin can turn blue.

More recently, a report has issued asserting that the application of urea and lactate was effective in reducing seborrheic keratosis which are said to melt away after several months.

Despite these continued efforts, there still remains a need for an effective, easy to apply, fast acting treatment for use in reducing or removing seborrheic keratoses. Most especially, there is a need for methods and treatments that can be used at home and purchased over-the-counter and which are free of, or substantially free of, undesirable side effects and which are effective with topical application for six weeks or less, preferably four weeks or less.

SUMMARY OF THE INVENTION

According to the first aspect of the present teaching there are provided topically applied compositions for the treatment of seborrheic keratosis which compositions comprises a) one or more, preferably a combination of, select antioxidants and/or antioxidant sources, most especially dietary antioxidants, alone or, preferably, in combination with b) one or more hydrating agents and/or c) one or more keratolytic agents. The select antioxidants/antioxidant sources are black walnut extract, rosemary essential oil, green tea extract, pomegranate extract, pomegranate juice extract, alma extract, licorice extract, licorice white extract, pumelo extract, citrus peel extract, poria extract, boswellia extract, and turmeric as well as the individual antioxidant components thereof and of other plant based extracts, especially food extracts, including hydroxy-1,4-naphthoquinones and/or the precursors and/or derivatives thereof, especially the hydro-, di-hydro-, and trihydroxy-precursors thereof; catechins, especially epigallocatechin gallate (EGCG), epigallocatechin (EGC), epicatechin gallate (ECG) and epicatechin (EC), isothiocyantes including 4-ethydisulfinyibutylisothiocynate; carnosol; carnosic acid; ursolic acid; rosmarinic acid; tannins; flavonoids; ellagic acid, allagetannic acid; anthocyanins ß-glucogallin, mucic acid, gallic acid, mucic acid gallates, including mucic acid 1,4-lactone 5-O gallate, mucic acid 1-methyl ester 2-O-gallate and mucic acid 6-O-gallate; glycyrrhizinic acid; glycyrrhetinic acid; glabridin; liquirtin; isoliquirtin; α-pinene; 1,8-cineole; camphor; borneaol; ferulic acid; camphene; linalool; d-limonene; apigenin; myrcene; caryopheyllene; lanotstane-type triterpenoids such as dehyrotumilosic acid; and boswellic acids such as 11-keto-boswellic acid, acetyl-11-keto-boswellic acid. While the preferred antioxidants and their precursors are the naturally occurring ones, i.e., extracts of various plants, seeds and fruits, e.g., in the case of black walnut extracts and their antioxidant components and precursors, extracts derived from the Juglandaceae family, synthetic antioxidants as well as the natural and synthetic precursors and derivatives corresponding to said preferred antioxidants are also suitable. Most preferably, these compositions will include suitable hydrating/humectant and/or keratolytic agents including, but not limited to, urea, salicylic acid, glycerin, lactate and salts thereof, especially zinc lactate. Typically, these treatment compositions, or the components thereof, will be incorporated into a cosmetically acceptable and/or a pharmaceutically acceptable carrier or excipient and/or as a component of a cosmetic composition and/or topically applied pharmaceutical composition for application to the afflicted skin.

The present teaching also pertains to a method of treating seborrheic keratosis which method comprises applying the aforesaid treatment composition or a topical composition comprising the same to seborrheic keratoses in an amount effective to reduce the size of or eliminate the seborrheic keratoses. Application may be with or without occlusion, though it is preferably with occlusion. The treatment is applied for a period of up to six, more typically for a period of up to four weeks. Longer application periods may be employed; however, there is oftentimes no or little benefit by the continued extended application periods. Furthermore, even when the application is ended after four or six weeks, oftentimes the seborrheic keratoses will continue to diminish.

The compositions according to the present teaching may, and preferably do, also comprise one or more cosmetic or pharmaceutical actives that supplement or facilitate the treatment of the seborrheic keratosis and/or counteract or mitigate any skin damage, discoloration, discomfort and/or inflammation of the skin caused by the treatment composition or its components. Especially preferred are hydrating agents, humectants, and exfoliants, keratolytic agents, and desquamation agents (the latter collectively referred to as keratolytic agents) including those mentioned above.

DESCRIPTION OF THE DRAWINGS

FIGS. 5A, 5B, 5C and 5D are photographs of the progression of diminution of the seborrheic keratoses in Case Study 5.

FIGS. 6A, 6B, 6C and 6D are photographs of the progression of diminution of the seborrheic keratoses in Case Study 6.

FIGS. 7A, 7B, 7C, 7D and 7E are photographs of the progression of diminution of the seborrheic keratoses in Case Study 7.

FIGS. 8A, 8B, 8C and 8D are photographs of the progression of diminution of the seborrheic keratoses in Case Study 8.

DETAIL DESCRIPTION OF THE INVENTION

Figure 1A:
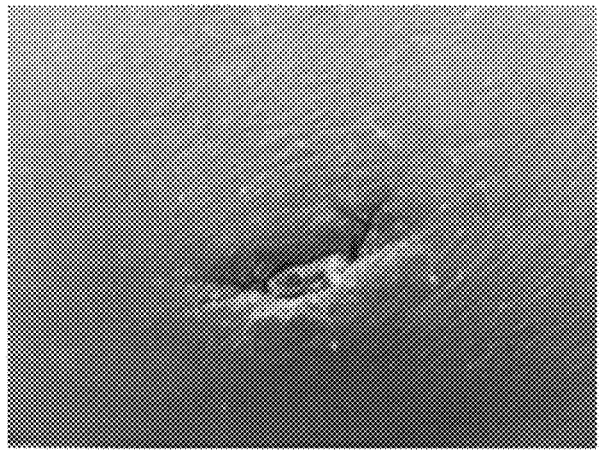
FIGS. 1A and 1B are photographs of the progression of diminution of the seborrheic keratoses in Case Study 1.

As used in the present specification and claims, the following terms shall have the meanings as presented:

"Pharmaceutically acceptable" means that the subject of this descriptor has been approved or is otherwise approvable by a regulatory agency of a government or governmental authority or is listed in the U.S. Pharmacopoeia or other generally recognized pharmacopoeia for use in animals, and more particularly in humans.

"Cosmetically acceptable" means that the subject of this descriptor has been accepted or otherwise acceptable for use in the cosmetic and skin care industry for skin contact.

"Treating" or "treatment" in relation to seborrheic keratosis refers to the diminution in the size, appearance, coloration and/or excision, exfoliation or sloughing off of the seborrheic keratosis.

"Optional" or "optionally" means that the subsequently described subject, event or circumstance may or may not occur, and that the description includes instances where the event occurs and instances where it does not and/or when the subject is present and when it is not present.

"Effective amount" refers to the amount of a compound or compositions that, when administered to seborrheic keratosis, is sufficient to effect a visible diminution in the size, appearance, and/or coloration and/or the ablation, exfoliation or sloughing off of the seborrheic keratosis. The "effective amount" can vary depending on, for example, the specific antioxidant or antioxidant combination or source thereof (i.e., extract) employed and the purity of the foregoing as well as the overall formulation of the composition to be applied. An appropriate amount in any given instance can be ascertained by those skilled in the art and/or is capable of determination by simple, routine experimentation.

"Natural" when used in relation to a compound or material refers to such compound or material that is partially or wholly isolated from or purified from a biological material. The partial or complete isolation or purification can be by any of a number of physical, chemical and/or other procedures known in the art. For purposes of this specification, a salt of the partially or wholly purified isolated compound or material is also to be considered a natural compound or material.

"Synthetic" when used in relation to a compound or material refers to such compound or material that is created or derived through chemical synthesis, chemical reaction, chemical derivation (as opposed to extraction from a biological material), biochemical conversion or the like, or combinations of the foregoing. A synthetic compound can be structurally the same as, or the chemical equivalent of, a natural compound and/or can be derived from a natural compound by synthetic processes.

"Extract" when used in relation to a biological organism, e.g., members of the Juglandaceae family, refers to both physical elements of the organism itself, such as ground, minced or chopped leaves, bark, roots, root bark, hulls (especially green hulls), seeds, seed pods, nuts, fruits, fruit peels (especially dried fruit peels), and the like, as well as extracts, as thought of traditionally, where the foregoing is subject to chemical processing whereby the desired chemical(s) is removed from the physical elements of the organism and recovered. Most preferably, the extracts used in accordance with the teaching of the present disclosure are of the latter type.

"Derivative" when used in reference to an antioxidant means both traditional derivatives which arise from a reaction or conversion from the given antioxidant as well as the precursors thereof which give rise to the select antioxidant as a result of a reaction, oxidation or conversion of the given precursor therefor. For example, in the case of 1,4-naphthoquinones, derivatives thereof include that arise from a reaction or conversion from the given 1,4-naphthoquione as well as the precursors thereof which give rise to the select 1,4-naphthoquinone as a result of a reaction, oxidation or conversion of the given precursor. Exemplary precursors of 1,4-naphthoquione include, for example, α- and β-hydrojuglone, 2,3-dihydro-1,4-naphthoquinone and 1,4,5-trihydroxy naphthalene and its glycoside.

Erring on the side of caution and in an effort to avoid having overlooked or inadvertently omitted certain descriptive matter, particularly complementary and supplementary descriptive matter, it is hereby stated and affirmed that the technical publications as well as the patent and patent application publications mentioned herein are all incorporated herein in their entirety by this reference. Indeed, for example, while the current specification could present page after page of description of suitable cosmetically acceptable and pharmaceutically acceptable vehicles, such would not be productive as the same are well known and well recognized by those skilled in the art and those that come into being subsequent to the filing of this application will readily be appreciated as suitable as well. The same holds true for many other potential constituents, both active and nonactive, that can be employed in topical compositions, especially topical skin treatments, cosmetics, creams, and the like, made in accordance with the present teachings.

According to the first aspect of the present teaching there are provided topically applied compositions for the treatment of seborrheic keratosis which compositions comprises a) one or more, preferably a combination of, select antioxidants and/or antioxidant sources, most especially dietary antioxidants, alone or, preferably, in combination with b) one or more hydrating and/or humectant agents and/or c) one or more keratolytic agents. Specifically, it has been found that topical compositions containing the aforementioned antioxidants and/or antioxidant sources, especially those further containing hydrating/humectant agents and/or keratolytic agents, are capable of reducing the size, appearance, coloration of the seborrheic keratoses and/or inducing or effecting the excision, exfoliation or sloughing off of the seborrheic keratosis. While other active agents known or found effective for treating seborrheic keratosis may be present, they are not necessary: though they supplement and may expedite the effect of the presently claimed seborrheic keratosis treatment composition.

In accordance with a second aspect of the present teaching there are provided topical compositions for treatment of seborrheic keratosis comprising A) a seborrheic keratosis treatment composition comprising a) one or more, preferably a combination of, select antioxidants and/or antioxidant sources, most especially dietary antioxidants, alone or, preferably, in combination with b) one or more hydrating and/or humectant agents and/or c) one or more keratolytic agents in B) a cosmetically acceptable and/or a pharmaceutically acceptable carrier or excipient and/or as a component of a cosmetic or other health and beauty aid composition and/or a topically applied pharmaceutical composition for application to the afflicted skin. The preferred seborrheic keratosis treatment component (A) consists essentially of a) one or more, preferably a combination of, dietary antioxidants and/or antioxidant sources, b) one or more hydrating agents/humectants and c) one or more keratolytic agents. Preferably, especially if the composition is to be applied with occlusion, the topical composition comprises the seborrheic keratosis treatment composition as the sole active component in a cosmetically acceptable and/or a pharmaceutically acceptable carrier or excipient since it is the desire of the individual applying the same to address the seborrheic keratosis and not other issues or skin conditions. Of course, if there is another skin malady affecting the same general area of the skin as the seborrheic keratosis, other pharmaceutical actives appropriate for that other malady will be incorporated into the topical composition as well. Alternatively, if the topical composition is to be applied without occlusion, then it is oftentimes desirable to incorporate the seborrheic keratosis treatment composition in a cosmetic composition which includes components designed to cover or mask the area treated, especially the visual prominence of the seborrheic keratoses.

Finally, according to yet another aspect of the present teaching there is provided a method for the treatment of seborrheic keratosis which method comprises applying to the seborrheic keratoses the seborrheic keratosis treatment composition, most especially a topical composition comprising the seborrheic keratosis treatment composition as described above and, in more detail, below.

The most critical component of the seborrheic keratosis treatment compositions of the present teaching is the antioxidant and/or antioxidant source, especially dietary antioxidants and antioxidant sources. While many dietary antioxidants and sources thereof are known and are known to affect many organs and operations of the body, including the skin, only select dietary antioxidants have been found suitable or efficacious for treating seborrheic keratosis. For example, resveratrol, n-acetyl cysteine, caffeic acid and lycopene, while effective agents in other human biological applications, were not found to improve the treatment of seborrheic keratosis. The select antioxidants/antioxidant sources suitable for use in the present teaching are Juglandaceae extracts, black walnut extract, rosemary essential oil, green tea extract, pomegranate extract, pomegranate juice extract, alma extract, licorice extract, licorice white extract, pumelo extract, citrus peel extract, poria extract, boswellia extract, and turmeric as well as the individual antioxidant components thereof and of other plant extracts, especially food extracts, including the hydroxy-1,4-naphthoquinones, especially the hydro-, di-hydro-, hydroxy- and trihydroxy-precursors thereof, including 5-hydroxy-1,4-naphthoquinone (juglone), 1,4,5-trihydroxynaphthalene and/or the glycosides or esters thereof, and 2,3-dihydro-5-hydroxy-1,4-naphthoquinone, most preferably 5-hydroxy-1,4-naphthoquinone; catechins, especially epigallocatechin gallate (EGCG), epigallocatechin (EGC), epicatechin gallate (ECG) and epicatechin (EC), isothiocyantes including 4-ethydisulfinylbutyl-isothiocynate; carnosol; carnosic acid; ursolic acid; rosmarinic acid; tannins; flavonoids; ellagic acid, allagetannic acid; anthocyanin; ß-glucogallin, mucic acid, gallic acid, mucic acid gallates, including mucic acid 1,4-lactone 5-O gallate, mucic acid 1-methyl ester 2-O-gallate and mucic acid 6-O-gallate; glycyrrhizinic acid; glycyrrhetinic acid; glabridin; liquirtin; isoliquirtin; α-pinene; 1,8-cineole; camphor; borneaol; ferulic acid; camphene; linalool; d-limonene apigenin; myrcene; caryopheyllene; lanotstane-type triterpenoids such as dehyrotumilosic acid; and boswellic acids such as 11-keto-boswellic acid, acetyl-11-keto-boswellic acid. While the preferred antioxidants and their precursors are the naturally occurring ones, i.e., extracts of various plants, seeds and fruits, e.g., in the case of black walnut extracts and their antioxidant components and precursors, extracts derived from the Juglandaceae family, synthetic antioxidants as well as the natural and synthetic precursors and derivatives corresponding to said preferred antioxidants are also suitable.

For convenience, rather than go into detail into each of the select antioxidants and antioxidant extracts, all of which are well known in the art, for exemplary purposes attention is now given to black walnut extract and, in particular, its key antioxidants. Specifically, one of the key antioxidants or groups of antioxidants suitable for use in the practice of the present teaching are the 1,4 naphthoquinones. Though these are attainable synthetically, most often they are derived from extracts of components (e.g., seed, fruit, fruit pod, bark, leaves, roots, etc.) of the Juglandaceae family, most especially extracts of the black walnut trees. The 1,4 naphthoquinones generally have the structure I

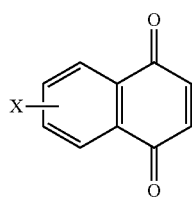

wherein X is hydrogen, hydroxyl, methyl, methoxy, quarternary amine, ketone, a $C_3$ to $C_7$ cycloalkyl, $C_2$ to $C_3$ alkyl, 1-alkylaminoalkyl, or alkanoyl groups or a pharmaceutically acceptable salt and/or derivatives thereof. Additional ring substitution can also be present as long as it does not adversely affect the effectiveness of the 1,4-naphthoquinone, i.e., additionally ring substitution can have no impact on or can alter, but not abolish, the seborrheic keratosis treatment activity of the 1,4-naphthoquinone. Exemplary additional ring substitutions include halogens, such as chlorine, bromine and fluorine, and oxygenated groups such as phosphates, nitrates, sulphates, or other groups or substituents such as methoxy, carboxy, carboxylate, carboxyl-lower alkyl, hydroxy, hydroxylates, quarternary amines, glucosyl, glucosylamine, or a variety of branched or straight chain alkyl groups, including methyl. In this respect, the additional ring substitution can be a useful means to increase or decrease solubility as necessary for the final topical formulation into which it is incorporated. As is apparent to one skilled in the art, a hydrophilic substituent should increase solubility in a water or aqueous based composition or component whereas a hydrophobic and/or lipophilic substituent should decrease solubility in a water or aqueous based composition or component and increase solubility in a lipophilic or oil based composition or component, respectively.

As noted, derivatives and precursors of the compounds of structure I can also be used. Such derivatives include those compounds of structure I in which one or both of the keto groups are substituted with a hydroxyl, glycoside or ester group. Additional derivatives that can be used are disclosed in, e.g., Stich et. al. (US Patent Application Publication US 2012/0322889). Preferably, the compounds according to structure I are 5-hydroxy-1,4-naphthoquinone (juglone), 1,4, 5-trihydroxynaphthalene and/or the glycosides or esters thereof, and 2,3-dihydro-5-hydroxy-1,4-naphthoquinone, most preferably 5-hydroxy-1,4-naphthoquinone.

As noted, suitable and preferred sources of the 1,4-naphthoquinone compounds and/or extracts containing the same are the plants and trees of the Juglandaceae family. These are well known and include the members of the *Juglans* genus including Japanese walnut, common walnut, black walnut, Manchurian walnut, white walnut, etc., many of which are identified in "Taschenbuch der Drogenkunde" by Heinz A. Hoppe, Walter de Gruyter, Berlin, N Y, 1981, pages 155-156; Hegnauer R., "Chemotaxonomie der Pflanzen" Volume IV, 1966, p. 281 and Hegnauer R., "Chemotaxonomie der Pflanzen" Volume Vill, 1989, p. 575. Preferred sources are *Juglans Regia* L. (common walnut) and *Juglans Nigra* L. (black walnut), most especially black walnut. Other members of the Juglandaceae family that serve as sources of the extract include the members of the *Carya* genus, e.g., pecan and hickory, especially the members of the pecan species. The extract may comprise or be prepared from the bark, roots (especially root bark), leaves, nuts, dried fruit peels, or hulls especially green hulls. When the extract comprises the physical elements of the plant, it is typically ground or comminuted to increase surface area such that the 1,4-naphthoquinone compound and/or derivative is readily released into the carrier or composition in which the material is combined for application to the skin. Most preferably, the extract is a traditional extract in which the desired 1,4-naphthoquinone and/or derivative is removed or isolated from the physical material of the plant, typically by solvent extraction, and recovered. Such processes are described in, for example, Wixforth (U.S. Pat. No. 5,137,717) and Mitchedlidze (U.S. Pat. No. 8,206,755). The purity of the extract, at least from the perspective of the desired 1,4-naphthoquinone or derivative content is not relevant so long as an effective amount is present when applied to the seborrheic keratosis. Generally, though, the extracts may be used as is, i.e., as results from the extraction process, or may be further purified and/or concentrated.

Again, those skilled in the art will readily appreciate the general applicability of the foregoing discussion with respect to the source and isolation of the 1,4-napthoquinones to the other extracts and individual antioxidants suitable for use in the practice of the present teachings, namely rosemary essential oil, green tea extract, pomegranate extract, pomegranate juice extract, alma extract, licorice extract, licorice white extract, pumelo extract, citrus peel extract, poria extract, boswellia extract, and turmeric as well as the individual antioxidant components thereof and of other plant extracts, especially food extracts, including the catechins, especially epigallocatechin gallate (EGCG), epigallocatechin (EGG), epicatechin gallate (ECG) and epicatechin (EC), isothiocyantes including 4-ethydisulfinylbutyl-isothiocynate; carnosol; carnosic acid; ursolic acid; rosmarinic acid; tannins; flavonoids; ellagic acid, allagetannic acid; anthocyanin; ß-glucogallin, mucic acid, gallic acid, mucic acid gallates, including mucic acid 1,4-lactone 5-O gallate, mucic acid 1-methyl ester 2-O-gallate and mucic acid 6-O-gallate; glycyrrhizinic acid; glycyrrhetinic acid; glabridin: liquirtin; isoliquirtin; α-pinene; 1,8-cineole; camphor; borneaol; ferulic acid; camphene; linalool; d-limonene; apigenin; nnyrcene; caryopheyllene; lanotstane-type triterpenoids such as dehyrotumilosic acid; and boswellic acids such as 11-keto-boswellic acid, acetyl-11-keto-boswellic acid.

Although effective compositions are prepared from the individual antioxidants, for example the 1,4-naphthoquinones, it is preferred that the compositions of the present teaching be prepared from combinations of such individual antioxidants, most preferably from the named extracts which typically include multiple individual antioxidants, as well as combinations of the named extracts or of one or more of the individual antioxidants with one or more of the named extracts. Specifically, it has been found that the combination of antioxidants, again especially those found within any given extract, provide enhanced effects as compared to the individual antioxidants themselves.

Again as noted, whether individual antioxidants or antioxidant sources are used, it is especially preferred that combinations of each or both be used, especially combinations of three or more. Indeed, it has been found that combinations of three or more antioxidant sources provide enhanced performance as compared to lesser antioxidants or use of the individual antioxidants. Preferred combinations of antioxidant sources include black walnut extract, green tea extract, pomegranate juice extract and turmeric; black walnut extract, green tea extract, pomegranate juice extract and rosemary essential oil; black walnut extract, green tea extract, pomegranate juice extract, turmeric and rosemary essential oil; black walnut extract, green tea extract, amla extract, rosemary extract and licorice extract; black walnut extract, green tea extract, amla extract and licorice; green tea extract, pomegranate juice extract and turmeric; green tea extract, pomegranate juice extract and rosemary essential oil; and green tea extract, pomegranate juice extract, turmeric and rosemary essential oil; green tea extract, amla extract, rosemary extract and licorice extract; green tea extract, and extract and licorice.

The amount of the antioxidant(s) and/or antioxidant source(e) be incorporated into the topical composition for use in the treatment of seborrheic keratosis is at least an effective amount. The specific amount will vary depending upon the purity thereof as well as, in part, the desired speed of efficacy and/or concerns for any detrimental effects associated with or arising from the select antioxidant(s) and/or antioxidant source(s), including their components and derivatives as well as any byproducts, contaminants, and the like contained therein or arising therefrom. For example, it is known that topical application of black walnut extract causes a skin darkening effect. Hence, it may be desirable to employ concentrations of such extracts which do not markedly affect skin coloration. On the other hand, since the skin color of the area of the skin underlying the seborrheic keratoses is oftentimes lighter than the adjacent skin, it may be desirable to use concentrations that do provide some level of skin coloration.

Generally speaking, the amount of the individual antioxidant or derivative (whether part of an extract or not) is present in an amount of from about 0.001 to about 10%, preferably from about 0.01 to 2%, by weight based on the total weight of the topical composition. Higher concentrations can be used but may lead to detrimental effects on the skin and, possibly, toxicity concerns. Notwithstanding the foregoing, it is to be appreciated that when an unpurified extract is employed, especially one which contains some or all of the plant matter itself, the amount of the desired antioxidant or derivative present therein is based on the content of the desired antioxidant or derivative itself, excluding the plant matter. For example, in the case of black walnut extract, one may incorporate 50% by weight of a an extract comprising 40% by weight finely ground walnut hull in a carrier such as a water/alcohol combination into a cosmetic carrier for an extract content of 20%; yet, the amount of 1,4-naphthoqinone or derivative is considerably less since the concentration of 1,4-naphthoqinone or derivative in the ground hull is typically just a few percent.

The preferred seborrheic keratosis treatment compositions according to present teaching comprise the aforementioned anitoxidants and/or antioxidant sources (or their derivatives and/or precursors) the contain one or more hydrating agents and/or one or more keratolytic agents, most preferably both. The make-up of these preferred seborrheic keratosis treatment compositions are typically 2 to 40%, preferably 5 to 30% most preferably 10 to 25% antioxidant or antioxidant sources; 30 to 90%, preferably 45 to 85% most preferably from 50 to 80% hydrating agent and from 0.5 to 20, preferably 1 to 15, most preferably from 2 to 10% keratolytic agent.

Preferably, though not necessarily, a plurality of antioxidants or antioxidant sources is employed in the preparation of these seborrheic keratosis treatment compositions. Again, the amount of any one antioxidant and/or antioxidant source depends upon the purity of the antioxidant or antioxidant source, the concentration of the antioxidants in the antioxidant source, the relative strength of each in facilitating the treatment of the seborrheic keratoses, etc. In general, individual antioxidants, especially those in a purer or concentrated form are present in an amount of 0.1 to 15%, preferably 1 to 10% whereas antioxidant sources, especially the less concentrated ones, are typically used in amount of from 2 to 30%, preferably 4 to 25%. Generally, speaking, the hydrating agents and keratolytic agents are present in amounts consistent for their typical use in cosmetic and skin care applications.

Suitable hydrating agents, especially those used in the skin care and cosmetics industries, are well known and typically characterized as humectants and/or moisturizers. Preferably the hydrating agent comprises one or more humectants, one or more moisturizers or a combination of both.

Humectants and moisturizers are typically characterized as being polyhydric alcohols, especially polyalkylene glycols and, more preferably, alkylene polyols and their derivatives. Exemplary humectants and moisturizers include propylene glycol, dipropylene glycol, polypropylene glycol, polyethylene glycol, 2-pyrrolidone-5-carboxylate, hydroxypropyl sorbitol, hexylene glycol, butylene glycol, ethoxydiglycol, 1,3-butylene glycol, 1,2,6-hexanetriol, triethylene glycol, glycerin, sugar alcohols (such as sorbitol, glycerol, xylitol, maltitol), urea, aloe vera gel, alpha hydroxy acids (such as lactic acid) and the metal salts thereof (such as zinc lactate), ß-glucans such as sodium carboxymethyl ß-glucan, glyceryl triacetate, polymeric polyols (such as polydextrose), glycerin, ethoxylated glycerin, propoxylated glycerin, compatible solutes, such as ectoin, hydroxectoin, taurines, camithine, acetyl camithine and mixtures thereof, etc.

Optionally, though again preferably, the seborrheic keratosis treatment compositions contain a keratolytic agent, i.e., exfoliants, keratolytic agents, and/or desquamation agents. As with the hydrating agents, keratolytic agents are well known in the skin care and cosmetic industry. Preferred keratolytic agents are the dermatological acids, including, but are not limited to, fatty acids, benzylic acids, hydroxy acids, keto acids, sugar acids and retinoids as well as analogs and combinations of the foregoing.

Suitable dermatological fatty acids include those fatty acids having one or more carboxyl (COOH) groups, particularly at least one carboxyl end group, and from 6 to 20 carbon atoms, inclusive of those of the carboxyl group. Suitable analogs include the lower alkyl esters thereof, e.g., the $C_1$ to $C_4$ alkyl esters, especially the ethyl esters. Exemplary dermatological fatty acids include azelaic acid, lauric acid, myristic acid, stearic acid, palmitic acid, arachidic acid, behenic acid, linoleic acid, alpha-linoleic acid, oleic acid, arachidonic acid, and the like.

Benzylic acids are generally of the formula (1):

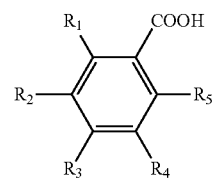

wherein $R_1$, $R_2$, $R_3$, $R_4$ and $R_5$ are each independently selected from the group consisting of H, OH, F, I Br, Cl, SH, $NH_2$, $C_{1-4}$ alkyl, $C_{1-4}$ alkoxyl, OR, COR, COOR, $CONR_2$ and $SO_3R$ wherein R is independently selected from H, $C_{1-4}$ alkyl and $C_{1-4}$ alkoxyl groups. Exemplary compounds of this formula include benzoic acid, 3-hydroxy benzoic acid, and salicylic acid.

Retinoids are compounds that are chemically related to vitamin A and generally include a cyclic group having a polyene side chain (typically having conjugated double bonds) with a polar end group. Suitable retinoids include first generation retinoids such as retinol, tretinoin, and isotretinoin; second generation retinoids such as etretinate and acitretin; and third generation retinoids such as tazarotene, adapalene and bexarotene. Especially useful retinoids include adapalene, tretinoin, isotretinoin, and tazarotene.

Sugar acids include the glyceric acids (acids based on glycerol), ascorbic acid, and glucuronic acid.

Hydroxy acids are aliphatic, cyclic, heterocyclic and aromatic carboxylic acids having at least one hydroxyl group in addition to the carboxylic group or groups. The most common hydroxy acids are the alpha- and beta-hydroxy acids, i.e., those hydroxy acids where the hydroxyl group is on the carbon atom next to or once removed from, respectively, the carboxyl carbon atom. Hydroxy acids may have a single hydroxyl group or a plurality of the same as well as a single carboxyl group or a plurality thereof. Furthermore, they may be used alone or in combination with other hydroxy acids or derivatives thereof, especially the simple esters (especially the $C_{1-4}$ alkyl esters) and ammonium salts thereof. Exemplary hydroxy acids include, but are not limited to: glycolic acid, lactic acid, citric acid, malic acid, tartaric acid, mandelic acid, gluconic acid, glycolic acid+ammonium glycolate, alpha-hydroxyethanoic acid+ammonium alpha-hydroxyethanoate, alpha-hydroxyoctanoic acid, alpha-hydroxycaprylic acid, hydroxycaprylic acid, mixed fruit acid, triple fruit acid, tri-alpha hydroxy fruit acids, sugar cane extract, alpha hydroxy and botanical complex, L-alpha hydroxy acid, salicylic acid, beta hydroxybutanoic acid, tropic acid, and trethocanic acid.

Other dermatological acids include, for example, trichloroacetic acid, the keto acids such as pyruvic acid and ethyl pyruvate, and the like.

Although the seborrheic keratosis treatment compositions and/or the preferred keratosis treatment compositions could be applied to the skin directly, they are most preferably applied as a component/as components of a topical composition comprising the seborrheic keratosis treatment composition in a cosmetically acceptable and/or a pharmaceutically acceptable carrier or excipient and/or as a component of a cosmetic composition and/or topically applied pharmaceutical composition. Preferably, the carriers or excipients are suitable for application, especially long term and repeated application, preferably under occlusion such as obtained with Nexcare or similar water-resistance bandage, to the skin without manifesting sensitization or irritation or inflammation. Generally speaking, the carrier or excipient will comprise from about 0.1 to about 99.999% by weight of the topical compositions, though when the preferred seborrheic keratosis treatment compositions are employed the carrier or excipient will comprise from about 0.1 to about 80%, preferably from about 20 to 70%, by weight of the topical compositions. Suitable carriers and excipients include any of the known topical excipients and like agents necessary for achieving the particular form of the skin care composition desired. Exemplary excipients include, e.g., mineral oils and emulsifying agents as well as water, alcohol, or water/alcohol combinations, or other solvent(s) or solvent systems in which the aforementioned actives may be, e.g., soluble, dispersed, emulsified, etc. Preferably, though, the skin care compositions will include excipients and the like that create a substantially stable, homogenous composition and/or provide body, improved partition coefficient, and viscosity to the composition so that the actives do not merely run off the skin once applied.

Generally speaking, any known carrier or base composition employed in traditional skin care/treatment compositions may be used in the practice of the present invention. Suitable carriers and carrier compositions are described at length in, for example, Gonzalez et. al.—U.S. Pat. No. 7,186,404; Aust et. al.—U.S. Pat. No. 7,175,834; Roseaver et. al.—U.S. Pat. No. 7,172,754; Simoulidis et. al.—U.S. Pat. No. 7,175,835; Mongiat et. al.—U.S. Pat. No. 7,101,536; Maniscalco—U.S. Pat. No. 7,078,022; Forestier et. al. U.S. Pat. Nos. 5,175,340, 5,567,418, 5,538,716, and 5,951,968; Deflandre et. al.—U.S. Pat. No. 5,670,140; Chaudhuri—U.S. Pat. Nos. 6,831,191, 6,602,515, 7,166,273, 6,936,735, and 6,699,463; Chaudhuri et. al.—U.S. Pat. Nos. 6,165,450 and 7,150,876; Bonda et. al. U.S. Pat. No. 6,962,692; Rodan et. al.—U.S. Pat. No. 9,144,434, Wang et. al. U.S. Pat. No. 5,830,441 and Auspitz et. al.—US 2007/0110685 A1. Those skilled in the art will readily recognize and appreciate what carriers may be employed in light of the intended form and/or delivery method for the seborrheic keratosis treating compositions.

The seborrheic keratosis treatment composition as well as the topical compositions are manufactured by means of conventional mixing, dissolving, granulating, dragee-making, levigating, encapsulation, and emulsifying processes. The topical compositions can be formulated in a conventional manner using one or more physiologically acceptable carriers, diluents, excipients, or auxiliaries, which facilitate processing of the seborrheic keratosis treatment composition or its components with one or more acceptable carriers or excipients. The topical compositions according to the present teaching can take the form of solutions, suspensions, emulsions, liquids, powders, creams, lotions, gels, sustained-release formulations, aerosols, sprays, or any other form suitable for topical administration to the skin. Most preferably, the seborrheic keratosis treatment composition as well as the topical compositions are in the form of alotion, cream, gel or the like which remains at the site of application. Lower viscosity compositions, e.g. liquid, solutions, suspensions, etc. may be used where the application site is to be occluded and the composition is wicked into or saturated into the occluding bandage or material.

Though a carrier by itself is sufficient for effecting the diminution or exfoliation of the seborrheic keratoses, it is preferable that the topical compositions of the present teaching include various other components typically associated with skin care/treatment products including, especially, cosmetic and/or pharmaceutical actives that supplement or facilitate the treatment of the seborrheic keratosis and/or counteract or mitigate any skin damage, discoloration, discomfort and/or inflammation of the skin treated with the seborrheic keratosis treatment composition. Such co-constituents include, but are not limited to antioxidants, sunscreens, skin lightening actives, vitamins, anti-inflammatory agents, compatible solutes, emollients and the like, and mixtures thereof, in their conventional amounts. Exemplary agents and additive materials are described briefly below as well as in the aforementioned patents, especially Maniscalco—U.S. Pat. No. 7,078,022. Each of these will be present in their conventional amount, though, as noted above and in the following examples, certain of these additives will manifest a synergy with the isohexides of the present application whereby the same performance may be realized with lesser amounts. In any event, such ingredients will typically be present in an amount of 1 to 30 wt %, preferably 2 to 20 wt %; though again, more active or highly active ingredients, like the sunscreen actives, antioxidants, anti-inflammatory agents, and the like are effective at levels as low as 0.01 wt %, preferably 0.1 wt %.

Suitable antioxidants include, but are not limited to, water-soluble antioxidants such as sulfhydryl compounds and their derivatives (e.g., sodium metabisulfite and N-acetyl-cysteine), lipoic acid, alpha lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, alkylresorcinols, meroterpenes, curcurmin and its derivatives and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, *Phyllanthus emblica, Terminalia chebula, Terminalia belerica,* and *Phyllanthus amarus.* Other examples of antioxidants may be found on pages 1612-13 of the ICI Handbook as well as in Ghosal—U.S. Pat. No. 6,124,288.

Since the skin being exposed following removal of the seborrheic keratoses is typically lighter than the adjacent skin, it is beneficial to include one or more sunscreen actives into the topical compositions. Both organic and inorganic sunscreen active can be used. Similarly, one can use sunscreen actives or combinations of sunscreen actives to protect against UV-A, UV—B or both. The amount of the sunscreen active to be incorporated into the sunscreen formulations is that which is conventional in the art. Typically, the amount is dependent upon, among other factors, the delivery means, e.g., is it applied as a spray or lotion; the stability of the active; the efficacy of the selected sunscreen active itself; and the application rate, as well as the particular SPF desired. From the commercial perspective, another factor influencing the level of such sunscreen actives in the sunscreen formulations is the regulatory limitations on their use. In the United States, for example, strict controls are placed upon the maximum level at which approved sunscreen actives may be present. Similar regulatory/governmental controls may also dictate which sunscreen actives may be used and at what amount in other countries as well.

Suitable organic sunscreen actives include, for example, avobenzone, butyl methoxydibenzoylmethane, cinoxate, benzophenone-8, dioxybenzone, homosalate, octylsalate, menthyl anthranilate, octocrylene, ethyhexyl methoxycinnamate, octyl methoxycinnamate, octyl salicylate, oxybenzone, padimate O, ethylhexyl salicylate, benzophenone-3, phenylbenzimidazole sulfonic acid, sulfisobezone, trolamine salicylate, 4-methylbenzylidene camphor, bisoctrizole, bemotrizinol, ecamsule, drometrizole trisiloxane, disodium phenyl dibenzimidazole tetrasulfonate, diethylamine hydroxybenzoyl hexyl bezoate, octyl triazone, hexyl benzoate, benzophenone-4, ethyhexyl triazone, diethylhexyl butamido triazone, bisimidazylate, polysilicone-15, etc. Suitable inorganic sunscreens include, but are not limited to, microfine surface treated titanium dioxide and microfine untreated and surface treated zinc oxide. Most preferably, if a sunscreen active is present, the topical compositions will comprise a combination of such sunscreen actives.

The skin care compositions of the present invention can also include one or more vitamins and/or their derivatives. Vitamins and vitamin derivatives include, for example, vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C and derivatives (for example ascorbyl palmitate, magnesium ascorbyl phosphate, ascorbyl acetate), vitamin D, ergocalciferol (vitamin $D_2$), vitamin E, DL-.alpha.-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$). Preferred vitamins are, for example, vitamin A palmitate, vitamin C and derivatives thereof, DL-$\alpha$-tocopherol, tocopherol E acetate, nicotinic acid, pantothenic acid and biotin. Vitamin E, which is often added to cosmetic and personal care products is also preferably stabilized by the compounds according to the invention. Additional preferred vitamins are Vitamin C and K and derivatives thereof.

The topical compositions may also include one or more amino acids and their derivatives. Amino acids and their derivatives include, for example, essential and non-essential amino acids and their derivatives. Eight amino acids are generally regarded as essential for humans: phenylalanine, valine, threonine, tryptophan, isoleucine, methionine, leucine, and lysine. Additionally, cysteine (or sulphur-containing amino acids), tyrosine (or aromatic amino acids), histidine and arginine are required by infants and growing children. Essential amino acids are so called not because they are more important to life than the others, but because the body does not synthesize them, making it essential to include them in one's diet in order to obtain them. In addition, the amino acids arginine, cysteine, glycine, glutamine, histidine, proline, serine and tyrosine are considered conditionally essential, meaning they are not normally required in the diet, but must be supplied exogenously to specific populations that do not synthesize it in adequate amounts. Amino acid derivatives may be simple esters or amides or complex peptides.

Suitable emollients that can be and preferably are incorporated into the topical compositions include those agents known for softening the skin which may be selected from hydrocarbons, fatty acids, fatty alcohols and esters. Petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following, triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric triglycerides, propylene glycol dicaprylate/dicaprate and decyl oleate.

Suitable anti-inflammatory ingredients include, but are not limited to, bisabolol, curcurmin and its derivatives, retinoids, flavonoids, meroterpenes (such as Bakuchiol or its derivatives) and other polyphenolics etc. These and other anti-inflammatory agents, as well as additional anti-oxidants and the like, are disclosed in Gupta et. al. (US 2005/0048008A1).

The topical compositions of the present teaching can also include one or more skin penetrants. These are additives that, when applied to the skin, have a direct effect on the permeability of the skin barrier: increasing the speed with which and/or the amount by which certain other compounds, especially those making up the seborrheic keratosis treatment composition, especially the antioxidants and/or antioxidant sources, are able to penetrate into the seborrheic keratoses. Exemplary organic penetration enhancers include dimethyl sulfoxide; dimethyl isosorbide, dimethyl isomannide, diethyl isoidide, diethyl isosorbide, diethyl isomannide, isopropyl isosorbide, isopropyl isomannide, isopropyl isoidide, isopropyl myristate; decyl, undecyl or dodecyl alcohol; propylene glycol; polyethylene glycol; $C_{9-11}$, $C_{12-13}$ or $C_{12-15}$ fatty alcohols; azone; alkyl pyrrolidones; lecithin; etc. Surfactants can also be used as penetration enhancers. When skin penetrants are employed it is important to endeavor to limit the application of the topical compositions to the seborrheic keratoses themselves and avoid other areas of the skin.

Other optional adjunct ingredients for the topical compositions of the present invention include preservatives, waterproofing agents, fragrances, anti-foam agents, plant extracts (Aloe vera, witch hazel, cucumber, etc), opacifiers, astingents, stabilizers, skin conditioning agents, colorants, and the like, each in amounts effective to accomplish their respective functions.

As evident from the foregoing, there is considerable overlap with respect to the performance or purpose thereof among the various components of the seborrheic keratosis treatment composition and the additives and optional ingredients that may be, and preferably are, employed in the compositions and methods of the present teaching. For example, urea is known to act as both a hydrating agent as well as a keratolytic agent. Similarly, there are many of the additive ingredients which have multiple performance capabilities.

As noted above, the present teaching also applies to a method of treating seborrheic keratosis by applying to the seborrheic keratoses the seborrheic keratosis treatment composition, most preferably a topical composition comprising the seborrheic keratosis treatment composition, with or without occlusion. The amount of the seborrheic keratosis treatment composition that is to be applied to the skin depends upon the amount of concentration and selection of ingredients of the seborrheic keratosis treatment composition as well as the form of the seborrheic keratosis treatment composition and its mode of application: typically it is an amount sufficient to wet and leave a thin film on the surface of the treated skin. Most especially, the seborrheic keratosis treatment composition is applied as a component of a topical composition, at least one having a carrier or solvent or excipient to aid in the application of the seborrheic keratosis treatment composition. Again, the amount to be applied likewise depends upon the amount of the seborrheic keratosis treatment composition in the topical composition as well as form of the topical composition. For example, a spray formulation may be applied so as to provide a light, even coat on the skin. Lotions, creams, gels and the like are typically applied at a rate of about 0.1 to about 10 mg/cm$^2$, preferably from about 1 to about 3 mg/cm$^2$, to the skin. This rate generally provides a thin even coating on the surface of the seborrheic keratoses. Regardless of the method of application, the key is to ensure the application of an effective amount of the antioxidant or antioxidant source or the seborrheic keratosis treatment composition.

The seborrheic keratosis treatment composition or topical compositions according to the present teaching are applied to the skin for so long a necessary to achieve the desired diminution of the seborrheic keratoses or, preferably, the complete removal thereof. Generally speaking, they are to be applied to the skin once, typically not more often than once, a day, with the preferred time of application following showering, bathing, swimming or any other activity which tends to result in the removal or wearing away of the previously applied composition. Of course, a second or more application may be necessary where such activity, i.e., showering, swimming, bathing, etc., follows the initial application on any given day. On the other hand, daily use is not required, especially if the individual or the treated area is not subject to conditions that cause the loss of the treatment. This may, however, lessen the efficacy or require longer application periods. However, if the treatment method calls for occlusion of the treated keratoses, it is only necessary to retreat periodically, perhaps every two to seven days, or as frequently as it becomes necessary to change the bandage or dressing. Generally speaking, it is not necessary to apply the seborrheic keratosis treatment composition or topical composition for more than six weeks, preferably no more than four weeks. Although the compositions could be applied for longer periods, such longer application is not found to improve the results. This is especially significant since alternative compositions, including those based on urea and lactic acid, are said to require several months of application to manifest the same results as seen with the present composition.

On the other hand, it is not always necessary to apply the compositions for the full four or six week period as it is also found that the benefits of the treatment continue even after application is terminated. As shown in the examples below, the seborrheic keratoses continue to diminish in size and/or appearance in the days and weeks following cessation of the application of the present compositions. Although not intended to be bound by theory, it is believed that the seborrheic treatment compositions initiated actions and/or effected degradation of the seborrheic keratoses which continued and/or whose effect was not fully manifested until after treatment had stopped.

EXAMPLES

Having described the invention in general terms, attention is now turned to the following pilot and case studies which demonstrate the efficacy of the present teachings. In each of the pilot studies and case studies 1 thru 4 a liquid herbal extract of black walnut green hulls of 1:1.75 wt.:vol. green hull:water-alcohol mixture (approx. 570 mg green hulls to 1 ml of solvent), hereinafter "BWE" for simplicity, was employed (Gaia Herbs, Inc., Brevard, NC). In each of case studies 5 thru 8 a topical composition in the form of a cream containing, as the antioxidant component, 5% green tea extract, 5% turmeric, 0.625% pomegranate extract and 0.625% rosemary essential oil; as the humectant, 12.5% urea (which also acts as a keratolytic agent), 10% glycerin, and 8.75% zinc lactate; and, as the keratolytic agent, 2.5% salicylic acid, was applied to seborrheic keratoses. The quantity applied was a pea-sized amount which generally provided a thin film of 3-4 mm over the surface of the seborrheic keratoses being treated. In all the case studies the treated area was occluded using a 3M Nexcare waterproof bandage (3M, St. Paul MN) following application of the treatment composition. The bandage was changed at typical internals of 3-9 days with a reapplication of the treatment composition. The patients were instructed to shower and exercise as normal but not scrub the area treated. At the time the bandage was removed an emery board is used to remove keratin slough and the old topical composition. Following removal, another quantity of the topical composition was applied and, again, the treated area occluded.

Pilot Study 1

A composition comprising BWE in a carrier was applied to SKs on a number of individuals. It was found that the treatment reduced the size of and/or resulted in the loss of the SKs.

Pilot Study 2

A composition comprising 20% BWE, 25% propylene glycol and 55% Aquaphor (Beiersdorf AG, Hamburg, Germany) was applied to the SKs of three patients. The SKs were found to have cleared from the skin after multiple days of application.

Case Study 1

Figure 1B:
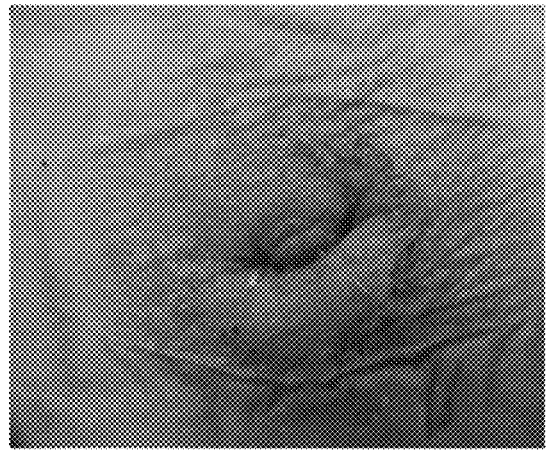

An 80-year-old female presented with a tender hyperkeratotic area on the nipple (FIG. 1A). A cream containing 7% zinc lactate and 10% urea was applied daily for 5 days without occlusion. No change in the keratosis was noted. Thereafter, a cream containing 20% BWE, 8% glycerin, 7% zinc lactate, 4% green tea extract, 4% turmeric, 0.5% pomegranate extract, and 0.5% rosemary was applied under occlusion for 7 days. Following removal of the bandage the central hyperkeratosis was found to be loosely attached and was extracted painlessly with a forceps, leaving the nipple free of hyperkeratosis (FIG. 1B). Telephone follow-up at 8 months confirmed that the lesion had not recurred.

Case Study 2

Figure 2A:
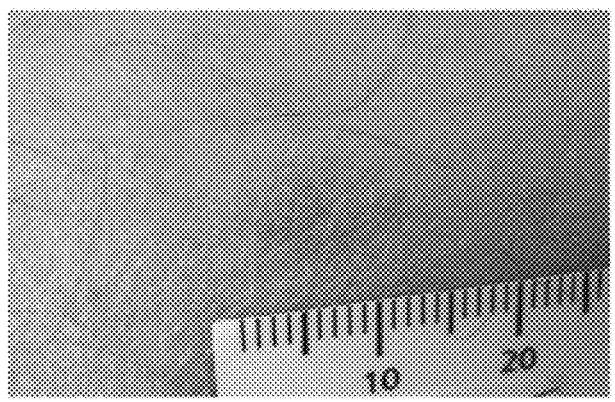
FIGS. 2A, 2B and 2C are photographs of the progression of diminution of the seborrheic keratoses in Case Study 2.
Figure 2B:
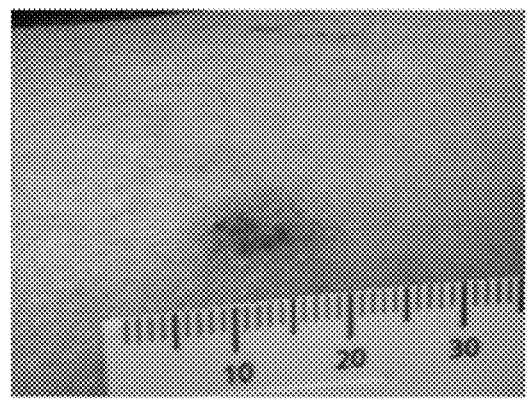
Figure 2C:
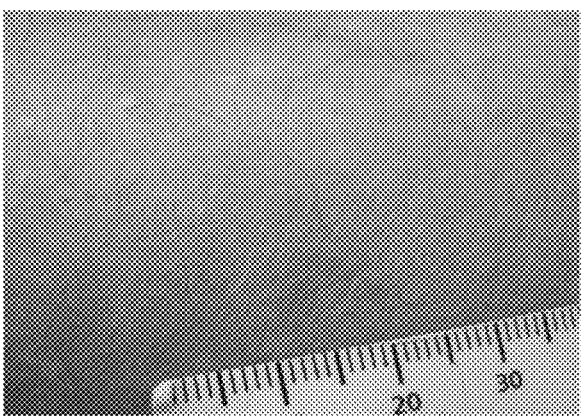

A 69-year-old male presented with an asymptomatic seborrheic keratosis on the lateral calf area (FIG. 2A). Following light debridement of the SK to remove loose cells with a pumice stone a thin coating of a cream containing 20% BWE, 10% urea, 8% glycerin, 7% zinc lactate, 4% green tea extract, 4% turmeric, 2% salicylic acid, 0.5% pomegranate extract, and 0.5% rosemary was applied to the SK and the treated area occluded. After 8 days the bandage was remove and the edge of an emery board used gently pry the dried cream and cells from the treated area. The SK was removed, though some capillary bleeding was noted (FIG. 2B). The lesion had not recurred 20 months later (FIG. 2C).

Case Study 3

Figure 3A:
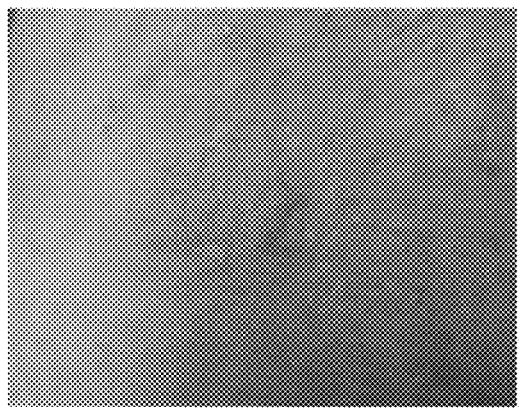
FIGS. 3A and 3B are photographs of the progression of diminution of the seborrheic keratoses in Case Study 3.

A 61-year-old female had a seborrheic keratosis on the extensor forearm (FIG. 3A). Debridement with a pumice stone was followed by application of the same formulation as in Case Study 2 and occlusion.

Figure 3B:
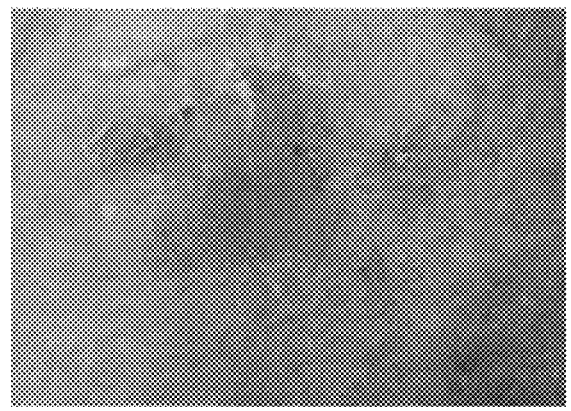

After one week the bandage removed and the dried cream and dead skin cells debrided with the edge of an emery board and the cream reapplied and the occlusive bandage replaced. After another week the bandage was removed and the dried cream and dead skin cells debrided. The SK was markedly reduced in size as seen in FIG. 3B.

Case Study 4

Figure 4A:
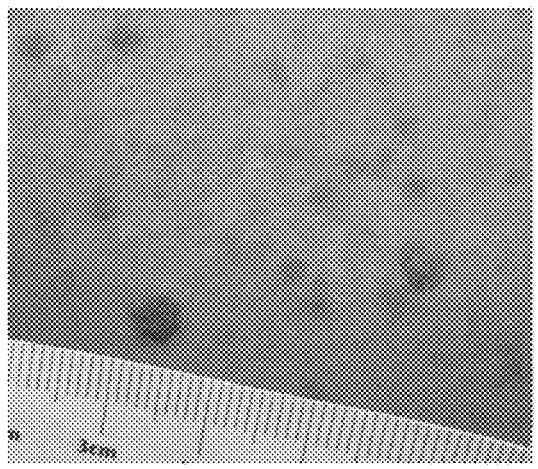
FIGS. 4A and 4B are photographs of the progression of diminution of the seborrheic keratoses in Case Study 4.
Figure 4B:
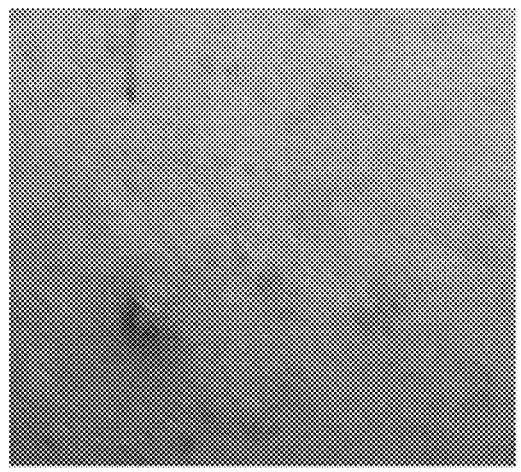

A 49-year-old female had two seborrheic keratoses on the medial thigh (FIG. 4A). The composition of Case Study 2 was applied and the treated area occluded. Application of the mixture and removal of the keratin slough at dressing changes with an emery board resulted in the disappearance or near disappearance of one SK and the marked reduction in size, prominence and color of the other by day 24 (FIG. 4B).

Case Study 5

A 64-year-old female presented with a SK on the left lateral thigh (FIG. 5A. Occlusion with the topical composition resulted in decreased thickness by Day 8 (FIG. 5B). Removal of keratin debris followed by 6 days more of occlusion with the topical composition led to further improvement by Day 14 (FIG. 5C). Another debridement resulted in further improvement (FIG. 5D).

Case Study 6

An 81-year-old female presented with an irritated SK on the lateral abdomen (FIG. 6A). Occlusion with the topical composition followed by keratin debris removal on Day 8 resulted in decreased thickness (FIG. 6B). Another 6 days of occlusion with the topical composition followed by keratin debris removal (Day 14) led to further improvement (FIG. 6C). Note superficial ulceration at right after keratin debris removal. The ulcer was healed after three days (Day 17, FIG. 6D). This area of the healed ulcer shows no residual SK; to the left, superficial SK remains.

Case Study 7

A 65-year-old female presented with a SK on the right calf (FIG. 7A). Occlusion with the topical composition resulted in decreased thickness by Day 8 (FIG. 7B). Removal of keratin debris followed by 7 days more of occlusion with the topical composition led to a small eschar by Day 15 (FIG. 7C). The lesion was allowed to heal, with no further treatment with the topical composition and no occlusion. Healing with erythema and a thin eschar is apparent by Day 22 (FIG. 7D). The SK was not apparent on Day 63 (FIG. 7E).

Case Study 8

The same 65-year-old female presented with a SK superior to the right popliteal area (FIG. 8A). Occlusion with the topical composition resulted in decreased thickness by Day 8 (FIG. 8B). Removal of keratin debris was followed by 7 days more of occlusion with the topical composition and debridement on Day 15 (FIG. 8C). The lesion was allowed to heal, with no further treatment with the topical composition and no occlusion. The SK was not apparent on Day 63 (FIG. 8D).

Exemplary Formulations

A number of formulary and performance observations were made in the various aforementioned pilot and case studies as well as additional variants thereof not reported here. For example, the addition of various natural antioxidants and combinations thereof, especially, green tea extract, turmeric, pomegranate extract, and rosemary were found to provide an enhanced, if not synergistic performance with the BWE. On the other hand, no visible improvement was seen with the addition of certain general antioxidants, namely, resveratrol, N-acetyl cysteine, caffeic acid and lycopene. Additionally, the addition of keratolytic agents and emollients appeared to help keep the composition from drying and improved the penetration of the composition into the SK. Similarly, it was found that a number of ingredients including urea, zinc lactate, salicylic acid and glycerin improved hydration as well as penetration into the SKs. Altogether, the addition of these additional ingredients as opposed to the BWE alone resulted in SKs that were softer at dressing change (2-7 days), enabling the moistened keratotic debris to be lifted from the skin with the edge of an emery board.

Four topical seborrheic keratosis treatment compositions were prepared according to the formulations presented in Table 1. Formulations A and C used deionized water whereas Formulations B and D used buffered water which was prepared by adding a 1.0% citric acid solution to water to QS pH 6.8. Otherwise these formulations were prepared by combining the ingredients of Phase 1 and heating to 70° C. A premix of Phase 2 was then added to the heated Phase 1 while mixing. Meanwhile the ingredients of Phase 3 were combined and heated to 70° C. and then added to the combined Phases 1 and 2 with mixing. Following the combination of Phase 1, 2 and 3, the mixture was homogenized until uniform after which the combination was allowed to cool to 45° C. At that point, a pre-mix of the ingredients of Phase 4 were added to the cooled mixture and the same further cooled to 30° C.

TABLE 1

| Phase | Ingredient/Commercial Name | A | B | C | D |
|---|---|---|---|---|---|
| 1 | Ultrez 30 | 1.00 | 1.0 | 1.00 | 0.5 |
|  | Water | 49.50 | 42.00 | 41.40 | 28.6 |
|  | Euxyl Pe9010 | 0.50 | 0.50 | 0.50 | 0.5 |
|  | Glycerin | 10.00 | 10.00 | 10.00 | 8.0 |
|  | AA26/Vitamin C |  | 2.00 |  |  |
|  | Black Walnut Extract |  |  |  | 15.0 |
| 2 | Rosemary extract/Rosemary CG, Sabinsa Corporation | 2.00 | 2.00 | 2.00 | 2.0 |
|  | Amla extract/Saberry antioxidant, Sabinsa Corporation | 2.00 | 2.00 | 2.00 | 2.0 |
|  | Green Tea extract/Sabinsa Corporation | 2.00 | 2.00 | 2.00 | 2.0 |
|  | Licorice extract/licorice CG, Sabinsa Corporation or ViaPure Licorize, Actives International | 2.00 | 2.00 | 2.00 | 2.0 |
|  | Ellagic acid |  | 2.00 | 2.00 | 2.0 |
|  | Co-Q10 |  | 3.00 | 2.00 | 2.0 |
|  | Ferulic acid/McKinley Resources |  |  | 0.50 | 0.5 |
|  | Poria extract/ViaPure poria, Actives International |  |  | 0.50 | 0.5 |
|  | Citrus extract/Citrus Sp/ ViaPure Citrus, Actives International |  |  | 0.10 | 0.1 |
|  | Boswellia extract/ViaPure Boswellia, Actives International |  |  | 0.20 | 0.2 |
|  | Beta-glucan/McKinley Resources |  |  | 0.20 | 0.2 |
| Phase 3 | Mantanov 82 | 4.00 | 4.00 | 4.00 | 4.00 |
|  | Glyceral stearate | 3.00 | 3.00 | 3.00 | 3.00 |
|  | Cetyl alcohol | 2.00 | 2.00 | 2.00 | 2.00 |
|  | Salicylic acid | 2.00 | 2.00 | 2.00 | 2.00 |
|  | Curcumonoids | 2.00 | 2.00 | 2.00 | 2.00 |
|  | Isopropyl myristate | 3.00 | 3.00 | 3.00 | 3.00 |
| Phase 4 | Urea | 10.00 | 10.00 | 10.00 | 10.00 |
|  | Zinc lactate | 5.00 | 5.00 | 5.00 | 5.0 |
|  | Vitamin E acetate |  | 0.50 | 0.50 | 0.50 |
|  | Vitamin C stabilized |  |  | 2.00 | 2.00 |
| Total |  | 100.00 | 100.00 | 100.00 | 100.00 |

Without further elaboration, it is believed that one skilled in the art, using the preceding description, can utilize the present invention to its fullest extent. Furthermore, while the present invention has been described with respect to aforementioned specific embodiments and examples, it should be appreciated that other embodiments, changes and modifications utilizing the concept of the present invention are possible, and within the skill of one in the art, without departing from the spirit and scope of the invention. The preceding preferred specific embodiments are, therefore, to be construed as merely illustrative, and not limitative of the remainder of the disclosure in any way whatsoever.

I claim:

1. A method of ameliorating the manifestation of seborrheic keratosis comprising applying to the surface of the seborrheic keratoses a topical composition comprising an effective amount of an antioxidant component, said antioxidant component comprising (i) one or more of a Juglandaceae extract, black walnut extract, and juglone, alone or in combination with (ii) two or more antioxidants or antioxidant sources selected from rosemary essential oil, green tea extract, pomegranate extract, pomegranate juice extract, amla extract, licorice extract, licorice white extract, pumelo extract, citrus peel extract, poria extract, boswellia extract, turmeric, catechins, isotiocyantes, carnosol, camosic acid, ursolic acid, rosmarinic acid, ellagic acid, anthocyanin, ß-glucogallin, gallic acid, glycyrrhizinic acid, glycyrrhetinic acid, glabridin, liquirtin, isoliquirtin, α-pinene, 1,8-cineole, ferulic acid, d-limonene, apigenin, caryopheyllene, lanotstane-type triterpenoids, and boswellic acids, said antioxidant component being applied topically to the seborrheic keratosis until the seborrheic keratosis is reduced in size or eliminated, with or without minor abrasion.

2. The method of claim 1 wherein component (ii) is present and includes at least three of rosemary essential oil, green tea extract, pomegranate extract, pomegranate juice extract, alma extract, licorice extract, licorice white extract, pumelo extract, citrus peel extract, pone extract, boswellia extract, ellagic acid, and turmeric.

3. The method of claim 2 wherein the antioxidant component (i) is black walnut extract.

4. The method of claim 1 wherein the antioxidant component (ii) is present and the antioxidant component further includes (iii) one or more of the following antioxidant or antioxidant sources: tannins, flavonoids, ellagetannic acid, mucic acid, mucic acid gallate, mucic acid 1,4-lactone 5-O gallate, mucic acid 1-methyl ester 2-O-gallate, mucic acid 6-O-gallate, epigallocatechin gallate (EGCG), epigallocatechin (EGC), epicatechin gallate (ECG), epicatechin (EC), 4-ethydisulfinylbutyl-isothiocynate, camphor, borneaol, camphene, linalool, and myrcene, caryopheyllene, dehyrotumilosic acid, 11-keto-boswellic acid and acetyl-11-ketoboswellic acid.

5. The method of claim 1 wherein the antioxidant component is or includes black walnut extract.

6. A method of ameliorating the manifestation of seborrheic keratosis comprising applying to the surface of the seborrheic keratoses an effective amount of a topical composition comprising a) an antioxidant component, b) one or more hydrating agents and c) one or more keratolytic agents wherein said antioxidant component is (i) one or more of a Juglandaceae extract, black walnut extract, and juglone, alone or in combination with (ii) two or more antioxidants or antioxidant sources selected from rosemary essential oil, green tea extract, pomegranate extract, pomegranate juice extract, amla extract, licorice extract, licorice white extract, pumelo extract, citrus peel extract, poria extract, boswellia extract, turmeric, catechins, isothiocyantes, carnosol, camosic acid, ursolic acid, rosmarinic acid, ellagic acid, anthocyanin, ß-glucogallin, gallic acid, glycyrrhizinic acid, glycyrrhetinic acid, glabridin, liquirtin, isoliquirtin, α-pinene, 1,8-cineole, ferulic acid, d-limonene, apigenin, caryopheyllene, lanotstane-type triterpenoids, and boswellic acids, said composition being applied topically to the seborrheic keratosis until the seborrheic keratosis is reduced in size or eliminated, with or without minor abrasion.

7. The method of claim 6 wherein the antioxidant component (ii) is present and includes at least three of rosemary essential oil, green tea extract, pomegranate extract, pomegranate juice extract, alma extract, licorice extract, licorice white extract, pumelo extract, citrus peel extract, poria extract, boswellia extract, ellagic acid, and turmeric.

8. The method of claim 7 wherein the antioxidant component (i) is black walnut extract.

9. The method of claim 7 wherein the antioxidant component (ii) is not present.

10. The method of claim 6 wherein the antioxidant component (ii) is present and the antioxidant component further includes (iii) one or more of the following antioxidant or antioxidant sources: tannins, flavonoids, ellagetannic acid, mucic acid, mucic acid gallate, mucic acid 1,4-lactone 5-O gallate, mucic acid 1-methyl ester 2-O-gallate, mucic acid 6-O-gallate, epigallocatechin gallate (EGCG), epigallocatechin (EGC), epicatechin gallate (ECG), epicatechin (EC), 4-ethydisulfinylbutyl-isothiocynate, camphor, borneaol, camphene, linalool, and myrcene, caryopheyllene, dehyrotumilosic acid, 11-keto-boswellic acid and acetyl-11-keto-boswellic acid.

11. The method of claim 6 wherein the antioxidant component is component (i) is or includes black walnut extract.

12. The method of claim 6 wherein the composition comprises 2 to 40% by weight of the antioxidant component (a), 30 to 90% by weight of the hydrating agent component (b), and 0.5 to 20% by weight of the keratolytic agent component (c), based on the combined weight of (a), (b) and (c); wherein each antioxidant or antioxidant source is present in an amount of from about 0.001 to about 10%.

13. The method of claim 12 wherein the topical composition further comprises from 0.1 to 80% by weight based on the total composition, of a cosmetically acceptable or pharmaceutically acceptable carrier or excipient.

14. A method of ameliorating the manifestation of seborrheic keratosis comprising applying to the surface of the seborrheic keratoses an effective amount of a topical composition comprising a) from 2 to 40% by weight of an antioxidant component comprising (i) at least one of Juglandaceae extract, black walnut extract, and juglone and (ii) two or more different, select antioxidants, each present in an amount of from 0.01-15% by weight, wherein the select antioxidants are selected from the group consisting of a rosemary essential oil, green tea extract, pomegranate extract, pomegranate extract, amla extract, licorice extract, licorice white extract, pumelo extract, citrus peel extract, citrus extract, boswellia extract, turmeric, catechins, rosmarinic acid, ellagic acid, poria extract, and boswellic acids, b) from 30 to 90% by weight of one or more hydrating agents and c) from 0.5 to 20% by weight of one or more keratolytic agents, said composition characterized as being more effective in reducing the size of and/or removing seborrheic keratosis as compared to the same formulation in the absence of the antioxidant component (a), the weight percent of the components based on the total weight of the combination of (a), (b) and (c); said composition being applied topically to the seborrheic keratosis until the seborrheic keratosis is reduced in size or eliminated, with or without minor abrasion.

15. The method of claim 14 wherein the antioxidant component (i) is black walnut extract.

16. The method of claim 14 wherein the antioxidant component (ii) is or includes at least two different select antioxidants selected from the group consisting of rosemary essential oil, green tea extract, pomegranate extract, pomegranate juice extract, alma extract, licorice extract, licorice white extract, citrus extract, ellagic acid, pumelo extract, citrus peel extract, boswellia extract and turmeric extract.

17. The method of claim 14 wherein the hydrating agents are selected from propylene glycol, dipropylene glycol, polypropylene glycol, polyethylene glycol, hydroxypropyl sorbitol, hexylene glycol, butylene glycol, ethoxydiglycol, 1,3-butylene glycol, 1,2,6-hexanetriol, triethylene glycol, glycerin, sorbitol, glycerol, xylitol, maltitol, urea, aloe vera gel, lactic acid zinc lactate, and mixtures thereof, etc.

18. The method of claim 14 wherein the keratolytic agents are selected from urea, fatty acids, benzylic acids, hydroxy acids, keto acids, sugar acids and retinoids as well as analogs and combinations of the foregoing.

19. The method of claim 14 wherein the composition further comprises from 0.1 to 80% by weight based on the total weight of the composition of a cosmetically acceptable or pharmaceutically acceptable carrier or excipient.

20. The method of claim 14 wherein the composition is applied with occlusion.

\* \* \* \* \*

UNITED STATES PATENT AND TRADEMARK OFFICE
CERTIFICATE OF CORRECTION

| | | |
|---|---|---|
| PATENT NO. | : 11,903,990 B2 | Page 1 of 1 |
| APPLICATION NO. | : 17/576922 | |
| DATED | : February 20, 2024 | |
| INVENTOR(S) | : William Van Dover Stoecker | |

It is certified that error appears in the above-identified patent and that said Letters Patent is hereby corrected as shown below:

In the Claims

Column 20, Line 13, Claim 1 the word "isotiocyanate" should be --isothiocyanate-- and the word "camosic" should be --carnosic--; at Column 20, Line 26, Claim 2 the word "pone" should be --poria--; and at Column 20, Line 57, Claim 6 the word "camosic" should be --carnosic--.

Signed and Sealed this
Twenty-first Day of May, 2024

Katherine Kelly Vidal
*Director of the United States Patent and Trademark Office*